United States Patent

Kurumatani et al.

[11] Patent Number: 6,127,413
[45] Date of Patent: Oct. 3, 2000

[54] OCULAR DEPRESSOR

[75] Inventors: Hajimu Kurumatani; Ayako Kawashima; Masafumi Isogaya; Hisanori Wakita, all of Kanagawa, Japan

[73] Assignee: Toray Industries, Inc., Tokyo, Japan

[21] Appl. No.: 08/875,022

[22] PCT Filed: Nov. 14, 1996

[86] PCT No.: PCT/JP96/03351

§ 371 Date: Oct. 15, 1997

§ 102(e) Date: Oct. 15, 1997

[87] PCT Pub. No.: WO97/17974

PCT Pub. Date: May 22, 1997

[30] Foreign Application Priority Data

Nov. 14, 1995 [JP] Japan ................................. 7-295789

[51] Int. Cl.$^7$ ........................ A61K 31/215; A61K 31/19
[52] U.S. Cl. ........................... 514/530; 514/573; 514/913
[58] Field of Search ........................ 514/530, 573, 514/913

[56] References Cited

PUBLICATIONS

Chemical Abstracts, 160:132287. Tsuji, 1986.

*Primary Examiner*—Zohreh Fay
*Attorney, Agent, or Firm*—Birch, Stewart, Kolasch & Birch, LLP

[57] ABSTRACT

This invention relates to an agent for decreasing ocular tension comprising as an effective ingredient a 4,8-inter-m-phenylene $PGI_2$ derivative represented by the formula:

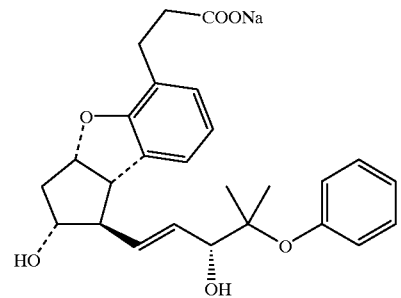

or a pharmaceutically acceptable salt thereof. The agent for decreasing ocular tension according to the present invention is useful as a therapeutic agent for treating various high ocular tension states such as glaucoma, ocular hypertension and high ocular tension which occurs after surgery.

3 Claims, 1 Drawing Sheet

OCULAR DEPRESSOR

This application is a 371 of PCT/JP96/03351 filed on Nov. 14, 1996.

TECHNICAL FIELD

The present invention relates to an agent for decreasing ocular tension comprising as an effective ingredient a prostaglandin $I_2$ derivative, 4,8-inter-m-phenylene prostaglandin $I_2$ derivative or a salt thereof.

BACKGROUND ART

Ocular tension is adjusted by the amount of aqueous humor filling the aqueous chambers. When the production of aqueous humor is increased or excretion of aqueous humor is inhibited, the ocular tension is increased. For example, glaucoma is an ophthalmic disease in which excavatio disci nervi optici and/or visual field defect is caused by the continues high ocular tension, which leads to blindness unless the high ocular tension is well cured. Further, in a type of glaucoma, various symptoms such as visual field defect occur under the ocular tension which is considered to be physiologically normal. It is thought that this is caused by the fact that pressure sensitivity of the visual nerves of the individual is high, and the disease is called low tension glaucoma. Inversely, some individuals show abnormally high ocular tensions while no clear lesions are observed in the visual nerves. This state is called hypertonia oculi or ocular hypertension. Agents for decreasing ocular tension are useful for therapy of various high ocular tension states such as glaucoma, ocular hypertension and high ocular tension which occurs after surgery.

In recent years, it was reported that prostaglandin-related compounds have activities to decrease ocular tension (13, 14-dihydro-15-keto-prostaglandins: Japanese Laid-open Patent Application (Kokai) No. 2-108; 13,14-dihydro-15(R) 17-phenyl-18,19,20-trinor prostaglandin $F_{2\alpha}$ ester: Japanese Laid-open Patent Application (Kokai) No. 6-500804), so that prostaglandins draw attention as drugs for decreasing ocular tension. It has been reported that prostaglandin $I_2$ ($PGI_2$, prostacyclin, Nature, Vol.268, p.688, 1976) and a derivative thereof, Iloprost (Philip F. J. Hoyng et al., 1989) have activities to decrease ocular tension in experimental animals.

However, it is known that prostaglandin $I_2$ and Iloprost cause transient increase in ocular tension and/or hyperemia. The object of the present invention is to provide an agent for decreasing ocular tension free from such side effects and has a high effectiveness.

$PGI_2$ has a drawback in that it is unstable in vivo so that its physiological activity does not last. $PGI_2$ derivatives with which this drawback is largely improved, which have a structure wherein the exoenol ether moiety is converted to inter-m-phenylene are described in Japanese Patent No. 1933167. It is known that these $PGI_2$ derivatives have a platelet aggregation-inhibition activity, vasodilating activity, gastric-acid secretion-inhibition activity, bronchodilating activity, uterine-contracting activity and the like.

DISCLOSURE OF THE INVENTION

To attain the above-mentioned object, the present invention provides a therapeutic agent for the diseases accompanied by increased ocular tension.

That is, the present invention includes the following inventions:

(1) An agent for decreasing ocular tension comprising as an effective ingredient a 4,8-inter-m-phenylene prostaglandin $I_2$ derivative of the formula (I):

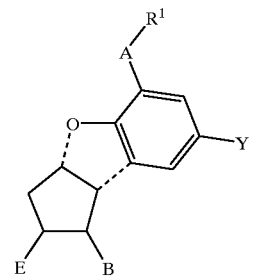

(wherein $R^1$ is
(A) $COOR^2$ wherein $R^2$ is
  1) hydrogen or a pharmaceutically acceptable cation,
  2) $C_1-C_{12}$ straight alkyl or $C_3-C_{14}$ branched alkyl,
  3) —Z—$R^3$
     wherein Z is valence bond or straight or branched alkylene represented by $C_tH_{2t}$ wherein t is an integer of 1–6; $R^3$ is a $C_3-C_{12}$ cycloalkyl or a $C_3-C_{12}$ substituted cycloalkyl substituted with 1–3 $R^4$ groups, wherein $R^4$ is hydrogen or $C_1-C_5$ alkyl,
  4) —(CH$_2$CH$_2$O)$_n$CH$_3$
     wherein n is an integer of 1–5,
  5) —Z—$Ar^1$
     wherein Z represents the same meaning as described above, $Ar^1$ is phenyl, α-naphthyl, β-naphthyl, 2-pyridyl, 3-pyridyl, 4-pyridyl, α-furyl, β-furyl, α-thienyl, β-thienyl or substituted phenyl (wherein substituent is at least one chlorine, bromine, fluorine, iodine, trifluoromethyl, $C_1-C_4$ alkyl, nitro, cyano, methoxy, phenyl, phenoxy, p-acetamidobenzamide, —CH=N—NH—C(=O)—NH$_2$, —NH—C(=O)—Ph, —NH—C(=O)—CH$_3$ or —NH—C(=O)—NH$_2$),
  6) —$C_tH_{2t}$COOR$^4$
     wherein $C_tH_{2t}$ and $R^4$ represent the same meanings as described above,
  7) —$C_tH_{2t}$N(R$^4$)$_2$
     wherein $C_tH_{2t}$ and $R^4$ represent the same meanings as described above,
  8) —CH(R$^5$)—C(=O)—R$^6$
     wherein $R^5$ is hydrogen or benzoyl, $R^6$ is phenyl, p-bromophenyl, p-chlorophenyl, p-biphenyl, p-nitrophenyl, p-benzamidophenyl, 2-naphthyl,
  9) —$C_pH_{2p}$—W—$R^7$
     wherein W is —CH=CH—, —CH=CR$^7$— or —C≡C—; $R^7$ is hydrogen or $C_1-C_{30}$ straight or branched alkyl or aralkyl; and p is an integer of 1–5, or
  10) —CH(CH$_2$OR$^8$)$_2$
      wherein $R^8$ is $C_1-C_{30}$ alkyl or acyl,
(B) —CH$_2$OH
(C) —C(=O)N(R$^9$)$_2$
   wherein $R^9$ is hydrogen, $C_1-C_{12}$ straight alkyl, $C_3-C_{12}$ branched alkyl, $C_3-C_{12}$ cycloalkyl, $C_4-C_{13}$ cycloalkylalkylene, phenyl, substituted phenyl (wherein substituents are the same as the substituents as in (A)5)) $C_7-C_{12}$ aralkyl or —SO$_2$R$^{10}$ wherein $R^{10}$ is $C_1-C_{10}$ alkyl, $C_3-C_{12}$ cycloalkyl, phenyl, substituted phenyl (wherein substituents are the same as the substituents as in (A)5)) or $C_7$–$C_{12}$ aralkyl, with the proviso that although the two $R^9$ groups may be the same or different, in cases where one of them is —$SO_2R^{10}$, the other is not —$SO_2R^{10}$, or (D) —$CH_2OTHP$ (wherein THP is tetrahydropyranyl group), A is
1) —$(CH_2)_m$—
2) —CH=CH—$CH_2$—
3) —$CH_2$—CH=CH—
4) —$CH_2$—O—$CH_2$—
5) —CH=CH—
6) —O—$CH_2$— or
7) —CH≡C—
wherein m is an integer of 1 or 2, Y is hydrogen, $C_1$–$C_4$ alkyl, chlorine, bromine, fluorine, formyl, methoxy or nitro, B is
—X—$C(R^{11})(R^{12})OR^{13}$
wherein $R^{11}$ is hydrogen or $C_1$–$C_4$ alkyl, $R^{13}$ is hydrogen, $C_1$–$C_{14}$ acyl, $C_6$–$C_{15}$ aroyl, tetrahydropyranyl, tetrahydrofuranyl, 1-ethoxyethyl or t-butyl, X is
1) —$CH_2$—$CH_2$—
2) —CH=CH— or
3) —C≡C—

$R^{12}$ is
1) $C_1$–$C_{12}$ straight alkyl, $C_3$–$C_{14}$ branched alkyl or
2) —Z—$Ar^2$
wherein Z represents the same meaning as described above, $Ar^2$ is phenyl, α-naphthyl, β-naphthyl, or at least one chlorine, bromine, fluorine, iodine, trifluoromethyl, $C_1$–$C_4$ alkyl, nitro, cyano, methoxy, phenyl or phenoxy-substituted phenyl, or
3) —$C_tH_{2t}OR^{14}$
wherein $C_tH_{2t}$ represents the same meaning as described above, $R^{14}$ is $C_1$–$C_6$ straight alkyl, $C_3$–$C_6$ branched alkyl, phenyl, at least one chlorine, bromine, fluorine, iodine, trifluoromethyl, $C_1$–$C_4$ alkyl, nitro, cyano, methoxy, phenyl or phenoxy-substituted phenyl, cyclopentyl, cyclohexyl, or cyclopentyl or cyclohexyl substituted with 1–4 $C_1$–$C_4$ straight alkyl groups, or
4) —Z—$R^3$
wherein Z and $R^3$ represent the same meanings as described above,
5) —$C_tH_{2t}$—CH=$C(R^{15})R^{16}$
wherein $C_tH_{2t}$ represents the same meaning as described above, $R^{15}$ and $R^{16}$ are hydrogen, methyl, ethyl, propyl or butyl, or
6) —$C_uH_{2u}$—C≡C—$R^{17}$
wherein u is an integer of 1–7, $C_uH_{2u}$ is straight or branched alkylene and $R^{17}$ is $C_1$–$C_6$ straight alkyl, E is hydrogen or —$OR^{18}$
wherein $R^{18}$ is $C_1$–$C_{12}$ acyl, $C_7$–$C_{15}$ aroyl or $R^2$
(wherein $R^2$ represents the same meaning as described above)

the formula (I) including d-isomer, l-isomer and dl-isomer) or a pharmaceutically acceptable salt thereof.

(2) An agent for decreasing ocular tension comprising as an effective ingredient the compound recited in (1) or a pharmaceutically acceptable salt thereof, wherein $R^1$ is
(A) $COOR^2$
wherein $R^2$ is
1) hydrogen or a pharmaceutically acceptable cation,
2) $C_1$–$C_{12}$ straight alkyl or $C_3$–$C_{14}$ branched alkyl, or
(B) —$CH_2OH$ A is
1) —$(CH_2)_m$—
2) —CH=CH— or
3) —O—$CH_2$—
wherein m is an integer of 1 or 2, Y is hydrogen, B is
—X—$C(R^{11})(R^{12})OR$—
wherein $R^{11}$ is hydrogen and $R^{13}$ is hydrogen, X is
1) —$CH_2$—$CH_2$— or
2) —CH=CH—

$R^{12}$ is
1) $C_1$–$C_{12}$ straight alkyl, $C_3$–$C_{14}$ branched alkyl, or
2) —Z—$Ar^2$
wherein Z represents the same meaning as described above, $Ar^2$ is phenyl, α-naphthyl, β-naphthyl, or at least one chlorine, bromine, fluorine, iodine, trifluoromethyl, $C_1$–$C_4$ alkyl, nitro, cyano, methoxy, phenyl or phenoxy-substituted phenyl, or
3) —$C_tH_{2t}OR^{14}$
wherein $C_tH_{2t}$ represents the same meaning as described above, $R^{14}$ is $C_1$–$C_6$ straight alkyl, $C_3$–$C_6$ branched alkyl, phenyl, at least one chlorine, bromine, fluorine, iodine, trifluoromethyl, $C_1$–$C_4$ alkyl, nitro, cyano, methoxy, phenyl or phenoxy-substituted phenyl, cyclopentyl, cyclohexyl, or cyclopentyl or cyclohexyl substituted with 1–4 $C_1$–$C_4$ straight alkyl groups, or
4) —$C_uH_{2u}$—C≡C—$R^{17}$
wherein u is an integer of 1–7, $C_uH_{2u}$ is straight or branched alkylene, and $R^{17}$ represents $C_1$–$C_6$ straight alkyl, and E is OH.

(3) The agent for decreasing ocular tension according to (1), wherein the disease accompanied by increased ocular tension is glaucoma, ocular hypertension or high ocular tension which occurs after surgery.

(4) A formulation comprising the compound recited in (1) and one or more other drugs having an ocular tension-decreasing activity.

(5) Use of the compound recited in (1) as a therapeutic agent for diseases accompanied by increased ocular tension.

(6) Use of the compound recited in (1) by administering the compound to a patient suffering from a disease accompanied by increased ocular tension.

(7) A method for treating a patient suffering from a disease accompanied by increased ocular tension, comprising administering to the patient the compound recited in (1).

The agent for decreasing ocular tension according to the present invention is useful for therapy of various high ocular tension states in glaucoma, ocular hypertension, high ocular tension which occurs after surgery or the like.

In cases where the compound according to the present invention is administered in the form of an eye drop, the compound is formulated into a solution with a concentration of usually 0.0001–0.5%, preferably 0.001–0.1%.

In cases where the agent for decreasing ocular tension according to the present invention is used in the form of eye drop, additives which are usually blended to eye drops may be added as required as long as they do not adversely affect the effect of the present invention. Usually, as the additives, buffers such as phosphate buffer; isotonizing agents such as sodium chloride and concentrated glycerin; antiseptics such as benzalkonium chloride; solubilizers (stabilizers) such as cyclodextrin; surfactants such as polysorbate 80; pH regulators such as sodium phosphate; thickeners such as carboxymethyl cellulose; chelating agents such as disodium edetate; and the like are used.

Since the agent for decreasing ocular tension according to the present invention has a stable chemical structure, there is no difficulties in formulating the compound. Therefore, in addition to the eye drop mentioned above, the compound may be formulated into an oral drug, injection solution, absorbefacient, external formulation such as ointment, and a suppository.

The formulation of the agent for decreasing ocular tension according to the present invention may contain another drug having an activity to decrease ocular tension. As the drug having an activity to decrease ocular tension, sympathomimetic such as epinephrine; sympathicolytic drugs such as timolol, parasympathomimetics such as pilocarpine; prostaglandin compounds such as isopropyl unoprostone; and the like are used.

BEST MODE FOR CARRYING OUT THE INVENTION

The ocular tension-decreasing action of the compounds of the above-described formula (I) will now be described concretely by way of examples. It should be noted, however, the present invention is not limited to the examples.

EXAMPLE 1

Ocular Tension-Decreasing Action

Using groups of New Zealand White rabbits having body weights of 2–4 kg, the ocular tension-decreasing action of the compounds of the formula (I) was tested, each group consisting of 2 or 3 rabbits. The compounds shown in Table 1 below were used as the test compounds. Further, for comparison, the action of $PGI_2$ was also tested.

To one eye, 30 μl of the test drug was administered and 30 μl of a solvent was administered to the other eye. The ocular tensions at 30 minutes to 6 hours after the administration were measured with ALCON APPLANATION PNEUMATONGRAPH electronic tonometer (ALCON JAPAN CO., LTD). When measuring the ocular tensions, 4% oxyprocaine was administered as a surface anesthetic. The test drugs were dissolved in the solvents shown in Tables 2 and 3.

Figure 1:
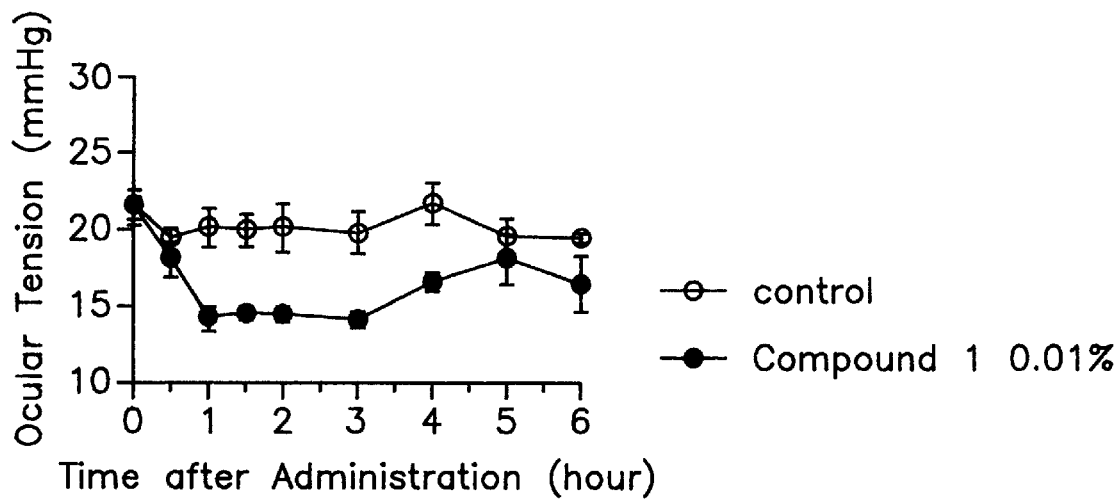
FIG. 1 is a graph showing the ocular tension-decreasing action of the compound according to the present invention.
Figure 2:
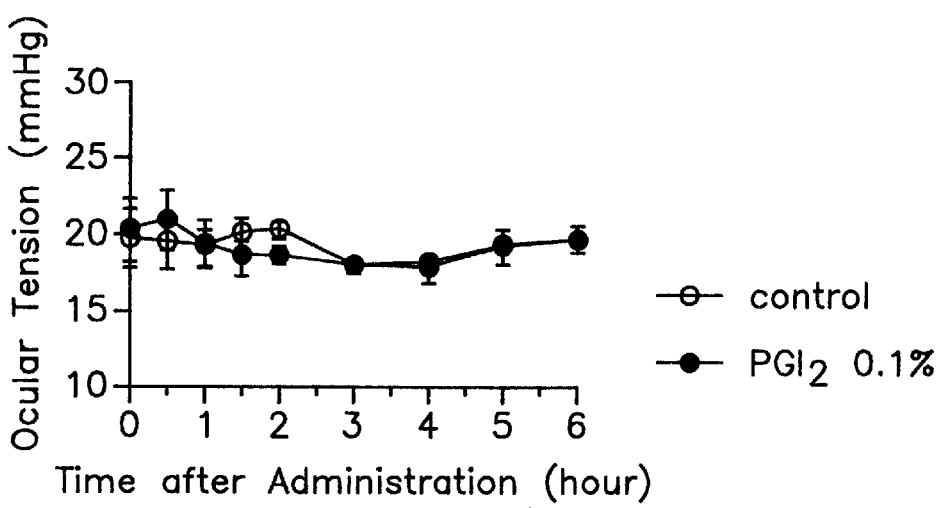
FIG. 2 is a graph showing the ocular tension-decreasing action of $PGI_2$.

FIG. 1 shows the change in ocular tension after administration of Compound 1 with time. Compound 1 decreased the ocular tension at the concentration of 0.01% and its maximum value was 7.3 mmHg. During this test, Compound 1 did not bring about the transient increase in ocular tension or hyperemia unlike the naturally occurring prostaglandins (Table 2). FIG. 2 shows the change in ocular tension after administration of $PGI_2$ with time. $PGI_2$ did not show ocular tension-decreasing action even at the concentration of 0.1%, and only hyperemia-causing action was observed (Table 2).

In Table 3, the ocular tension-decreasing actions of the compounds of the present invention shown in Table 1 other than Compound 1 are shown.

TABLE 1

| Compound 1 | A | $-(CH_2)_2-$ |
| | $R^1$ | $-COCNa$ |
| | Y | $-H$ |
| | B | (structure: CH=CH-CH(OH)-C(CH_3)_2-O-phenyl) |
| | E | ''''''OH |
| Compound 2 | A | $-(CH_2)_2-$ |
| | $R^1$ | $-COOCH_3$ |
| | Y | $-H$ |
| | B | (structure: CH=CH-CH(OH)-C(CH_3)_2-O-phenyl) |
| | E | ''''''OH |
| Compound 3 | A | $-(CH_2)_2-$ |
| | $R^1$ | $-COOH$ |
| | Y | $-H$ |
| | B | (structure: CH_2-CH_2-CH(OH)-C(CH_3)_2-O-phenyl) |
| | E | ''''''OH |
| Compound 4 | A | $-O-CH_2-$ |
| | $R^1$ | $-COOH$ |
| | Y | $-H$ |
| | B | (structure: CH=CH-CH(OH)-C(CH_3)_2-O-phenyl) |
| | E | ''''''OH |
| Compound 5 | A | $-O-CH_2-$ |
| | $R^1$ | $-COOH$ |
| | Y | $-H$ |
| | B | (structure: CH=CH-CH(OH)-CH(CH_3)-CH_2-CH_2-CH_3) |
| | E | ''''''OH |

TABLE 1-continued

| Compound 6 | A | —(CH$_2$)$_2$— |
| --- | --- | --- |
| | R$^1$ | —CH$_2$OH |
| | Y | —H |
| | B | 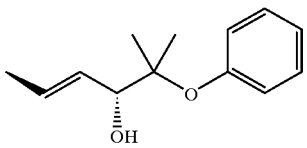 |
| | E | ⫶⫶⫶OH |
| Compound 7 | A | —(CH$_2$)$_2$— |
| | R$^1$ | —COOH |
| | Y | —H |
| | B | 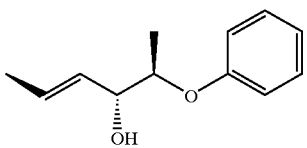 |
| | E | ⫶⫶⫶OH |
| Compound 8 | A | —O—CH$_2$— |
| | R$^1$ | —COOH |
| | Y | —H |
| | B | 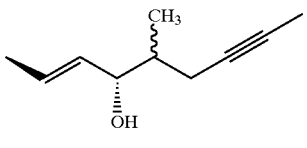 |
| | E | ⫶⫶⫶OH |
| Compound 9 | A | —(CH$_2$)$_2$— |
| | R$^1$ | —COOH |
| | Y | —H |
| | B | 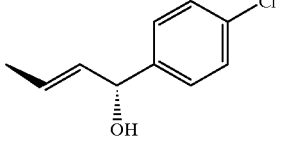 |
| | E | ⫶⫶⫶OH |
| Compound 10 | A | —CH=CH— |
| | R$^1$ | —CH$_2$OH |
| | Y | —H |
| | B | 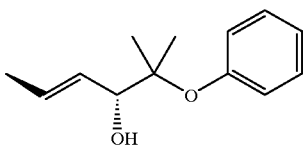 |
| | E | ⫶⫶⫶OH |
| Compound 11 | A | —O—CH$_2$— |
| | R$^1$ | —COOH |
| | Y | —H |

TABLE 1-continued

| | B | 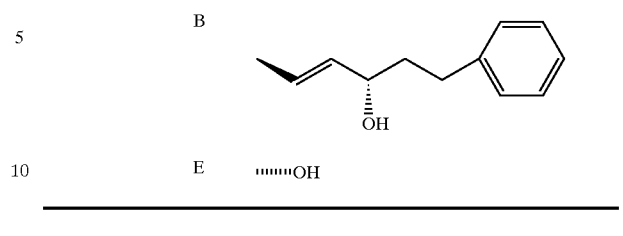 |
| --- | --- | --- |
| | E | ⫶⫶⫶OH |

TABLE 2

| Compound | Solvent | Concentration | Number of Animals Which Showed Hyperemia |
| --- | --- | --- | --- |
| Compound 1 | 100 mM phosphate buffer | 0.01% | 0 |
| PGI$_2$ | 100 mM carbonate buffer | 0.1% | 3 |

TABLE 3

| Test Compound | Solvent | Concentration | Maximum Decrease in Ocular Tension (mmHg) |
| --- | --- | --- | --- |
| Compound 2 | 2% polysorbate 80 | 0.001 | 5.9 |
| Compound 3 | 100 mM phosphate buffer | 0.1 | 4.1 |
| Compound 4 | 100 mM phosphate buffer | 0.001 | 6.4 |
| Compound 5 | 100 mM phosphate buffer | 0.01 | 6.7 |
| Compound 6 | 2% polysorbate 80 | 0.01 | 5.9 |
| Compound 7 | 100 mM phosphate buffer | 0.01 | 1.1 |
| Compound 8 | 100 mM phosphate buffer | 0.01 | 2.6 |
| Compound 9 | 100 mM phosphate buffer | 0.01 | 4.2 |
| Compound 10 | 2% polysorbate 80 | 0.01 | 3.6 |
| Compound 11 | 100 mM phosphate buffer | 0.01 | 2.7 |

Industrial Availability

The 4,8-inter-m-phenylene prostaglandin I$_2$ derivatives according to the present invention have excellent pharmacological effects and do not cause transient increase in ocular tension and/or hyperemia, so that they are useful as the agents for decreasing ocular tension.

What is claimed is:

1. A method for treating a patient suffering from a disease accompanied by increased ocular tension, comprising administering to the patient a therapeutically effective amount of a 4,8-inter-m-phenylene prostaglandin I$_2$ derivative of the following formula (I):

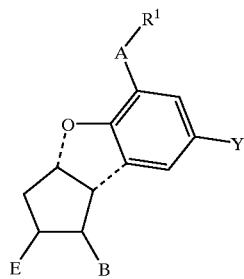

(wherein R¹ is
(A) COOR² wherein R² is
1) hydrogen or a pharmaceutically acceptable cation,
2) $C_1$–$C_{12}$ straight alkyl or $C_3$–$C_{14}$ branched alkyl,
3) —Z—R³
   wherein Z is valence bond or straight or branched alkylene represented by $C_tH_{2t}$, wherein t is an integer of 1–6; R³ is a $C_3$–$C_{12}$ cycloalkyl or a $C_3$–$C_{12}$ substituted cycloalkyl substituted with 1–3 R⁴ groups, wherein R⁴ is hydrogen or $C_1$–$C_5$ alkyl,
4) —(CH₂CH₂O)$_n$CH₃
   wherein n is an integer of 1–5,
5) —Z—Ar¹
   wherein Z represents the same meaning as described above, Ar¹ is phenyl, α-naphthyl, β-naphthyl, 2-pyridyl, 3-pyridyl, 4-pyridyl, α-furyl, β-furyl, α-thienyl, β-thienyl or substituted phenyl (wherein substituent is at least one chlorine, bromine, fluorine, iodine, trifluoromethyl, $C_1$–$C_4$ alkyl, nitro, cyano, methoxy, phenyl, phenoxy, p-acetamidobenzamide, —CH=N—NH—C(=O)—NH₂, —NH—C(=O)—Ph, —NH—C(=O)—CH₃ or —NH—C(=O)—NH₂),
6) —$C_tH_{2t}$COOR⁴
   wherein $C_tH_{2t}$ and R⁴ represent the same meanings as described above,
7) —$C_tH_{2t}$N(R⁴)₂
   wherein $C_tH_{2t}$ and R⁴ represent the same meanings as described above,
8) —CH(R⁵)—C(=O)—R⁶
   wherein R⁵ is hydrogen or benzoyl, R⁶ is phenyl, p-bromophenyl, p-chlorophenyl, p-biphenyl, p-nitrophenyl, p-benzamidophenyl, 2-naphthyl,
9) —$C_pH_{2p}$—W—R⁷
   wherein W is —CH=CH—, —CH=CR⁷— or —C≡C—; R⁷ is hydrogen or $C_1$–$C_{30}$ straight or branched alkyl or aralkyl; and p is an integer of 1–5, or
10) —CH(CH₂OR⁸)₂
    wherein R⁸ is $C_1$–$C_{30}$ alkyl or acyl,
(B) —CH₂OH
(C) —C(=O)N(R⁹)₂
    wherein R⁹ is hydrogen, $C_1$–$C_{12}$ straight alkyl, $C_3$–$C_{12}$ branched alkyl, $C_3$–$C_{12}$ cycloalkyl, $C_4$–$C_{13}$ cycloalkylalkylene, phenyl, substituted phenyl (wherein substituents are the same as the substituents as in (A)5)), $C_7$–$C_{12}$ aralkyl or —SO₂R¹⁰ wherein R¹⁰ is $C_1$–$C_{10}$ alkyl, $C_3$–$C_{12}$ cycloalkyl, phenyl, substituted phenyl (wherein substituents are the same as the substituents as in (A)5)) or $C_7$–$C_{12}$ aralkyl, with the proviso that although the two R⁹ groups may be the same or different, in cases where one of them is —SO₂R¹⁰, the other is not —SO₂R¹⁰, or (D) —CH₂OTHP (wherein THP is tetrahydropyranyl group), A is
1) —(CH₂)$_m$—
2) —CH=CH—CH₂—
3) —CH₂—CH=CH—
4) —CH₂—O—CH₂—
5) —CH=CH—
6) —O—CH₂— or
7) —C≡C—
   wherein m is an integer of 1 or 2, Y is hydrogen, $C_1$–$C_4$ alkyl, chlorine, bromine, fluorine, formyl, methoxy or nitro, B is
—X—C(R¹¹)(R¹²)OR¹³
wherein R¹¹ is hydrogen or $C_1$–$C_4$ alkyl, R¹³ is hydrogen, $C_1$–$C_{14}$ acyl, $C_6$–$C_{15}$ aroyl, tetrahydropyranyl, tetrahydrofuranyl, 1-ethoxyethyl or t-butyl, X is
1) —CH₂—CH₂—
2) —CH=CH— or
3) —C≡C—

R¹² is
1) $C_1$–$C_{12}$ straight alkyl, $C_3$–$C_{14}$ branched alkyl or
2) —Z—Ar²
   wherein Z represents the same meaning as described above, Ar² is phenyl, α-naphthyl, β-naphthyl, or at least one chlorine, bromine, fluorine, iodine, trifluoromethyl, $C_1$–$C_4$ alkyl, nitro, cyano, methoxy, phenyl or phenoxy-substituted phenyl, or
3) —$C_tH_{2t}$OR¹⁴
   wherein $C_tH_{2t}$ represents the same meaning as described above, R¹⁴ is $C_1$–$C_6$ straight alkyl, $C_3$–$C_6$ branched alkyl, phenyl, at least one chlorine, bromine, fluorine, iodine, trifluoromethyl, $C_1$–$C_4$ alkyl, nitro, cyano, methoxy, phenyl or phenoxy-substituted phenyl, cyclopentyl, cyclohexyl, or cyclopentyl or cyclohexyl substituted with 1–4 $C_1$–$C_4$ straight alkyl groups, or
4) —Z—R³
   wherein Z and R³ represent the same meanings as described above,
5) —$C_tH_{2t}$—CH=C(R¹⁵)R¹⁶
   wherein —$C_tH_{2t}$ represents the same meaning as described above, R¹⁵ and R¹⁶ are hydrogen, methyl, ethyl, propyl or butyl, or
6) —$C_uH_{2u}$—C≡C—R¹⁷
   wherein u is an integer of 1–7, $C_uH_{2u}$ is straight or branched alkylene and R¹⁷ is $C_1$–$C_6$ straight alkyl, E is hydrogen or —OR¹⁸
wherein R¹⁸ is $C_1$–$C_{12}$ acyl, $C_7$–$C_{15}$ aroyl or R²
(wherein R² represents the same meaning as described above) the formula (I) including d-isomer, l-isomer and dl-isomer) or a pharmaceutically acceptable salt thereof, and a pharmaceutically acceptable carrier.

2. The method according to claim 1, wherein said disease accompanied by increased ocular tension is glaucoma, ocular hypertension or high ocular tension that occurs after surgery.

3. The method according to claim 1, wherein in formula (I), $R^1$ is
- (A) $COOR^2$
  wherein $R^2$ is
  1) hydrogen or a pharmaceutically acceptable cation,
  2) $C_1$–$C_{12}$ straight alkyl or $C_3$–$C_{14}$ branched alkyl, or
- (B) —$CH_2OH$ A is
1) —$(CH_2)_m$—
2) —CH═CH— or
3) —O—$CH_2$—
wherein m is an integer of 1 or 2, Y is hydrogen, B is
—X—$C(R^{11})(R^{12})OR^{13}$
wherein $R^{12}$ is hydrogen and $R^{13}$ is hydrogen,
X is
1) —$CH_2$—$CH_2$— or
2) —CH═CH—
$R^{12}$ is
1) $C_1$–$C_{12}$ straight alkyl, $C_3$–$C_{14}$ branched alkyl, or
2) —Z—$Ar^2$ wherein Z represents the same meaning as described above, $Ar^2$ is phenyl, α-naphthyl, β-naphthyl, or at least one chlorine, bromine, fluorine, iodine, trifluoromethyl, $C_1$–$C_4$ alkyl, nitro, cyano, methoxy, phenyl or phenoxy-substituted phenyl, or 3) —$C_tH_{2t}OR^{14}$
wherein $C_tH_{2t}$ represents the same meaning as described above, $R^{14}$ is $C_1$–$C_6$ straight alkyl, $C_3$–$C_6$ branched alkyl, phenyl, at least one chlorine, bromine, fluorine, iodine, trifluoromethyl, $C_1$–$C_4$ alkyl, nitro, cyano, methoxy, phenyl or phenoxy-substituted phenyl, cyclopentyl, cyclohexyl, or cyclopentyl or cyclohexyl substituted with 1–4 $C_1$–$C_4$ straight alkyl groups, or 4) —$C_uH_{2u}$—C≡C—$R^{17}$
wherein u is an integer of 1–7, $C_uH_{2u}$ is straight or branched alkylene, and $R^{17}$ represents $C_1$–$C_6$ straight alkyl, and E is OH.

* * * * *